(12) United States Patent
Canham et al.

(10) Patent No.: US 9,540,246 B2
(45) Date of Patent: Jan. 10, 2017

(54) POROUS SILICON (75) Inventors: Leigh Trevor Canham, Worcestershire (GB); Armando Loni, Herefordshire (GB)

(73) Assignee: PSIMEDICA LIMITED, Worcestershire (GB)

( * ) Notice: Subject to any disclaimer, the term of this patent is extended or adjusted under 35 U.S.C. 154(b) by 0 days.

(21) Appl. No.: 13/516,881

(22) PCT Filed: Dec. 16, 2010

(86) PCT No.: PCT/GB2010/052112
§ 371 (c)(1),
(2), (4) Date: Sep. 28, 2012

(87) PCT Pub. No.: WO2011/073666
PCT Pub. Date: Jun. 23, 2011

(65) Prior Publication Data
US 2013/0034714 A1 Feb. 7, 2013

(30) Foreign Application Priority Data

Dec. 17, 2009 (GB) .................. 0922063.3

(51) Int. Cl.
*C01B 33/02* (2006.01)
*A23L 1/03* (2006.01)
*A61K 8/25* (2006.01)
*A61Q 19/00* (2006.01)
*B44C 1/22* (2006.01)

(52) U.S. Cl.
CPC .............. *C01B 33/02* (2013.01); *A23L 1/0305* (2013.01); *A61K 8/25* (2013.01); *A61Q 19/00* (2013.01); *A61K 2800/413* (2013.01); *B44C 1/22* (2013.01); *C01P 2004/51* (2013.01); *C01P 2006/12* (2013.01); *C01P 2006/14* (2013.01)

(58) Field of Classification Search
CPC .................................. C01B 33/02; B44C 1/22
USPC ............................................................ 216/56
See application file for complete search history.

(56) References Cited

U.S. PATENT DOCUMENTS

| | | | |
|---|---|---|---|
| 6,929,950 B2 * | 8/2005 | Canham et al. | 435/459 |
| 7,244,513 B2 | 7/2007 | Li et al. | |
| 7,514,369 B2 * | 4/2009 | Li et al. | 438/753 |
| 7,560,085 B2 | 7/2009 | Farrell et al. | |
| 2004/0076813 A1 | 4/2004 | Han et al. | |
| 2004/0166319 A1 | 8/2004 | Li et al. | |
| 2006/0251561 A1 | 11/2006 | Farrell et al. | |
| 2006/0251562 A1 | 11/2006 | Farrell et al. | |
| 2007/0237979 A1 | 10/2007 | Li et al. | |

(Continued)

FOREIGN PATENT DOCUMENTS

| | | |
|---|---|---|
| JP | 2008-536906 | 9/2008 |
| WO | 2006-111761 | 10/2006 |
| WO | WO 2006/121870 | 11/2006 |
| WO | WO 2010/139987 | 12/2010 |

OTHER PUBLICATIONS

Stain Etching with Fe(III), V(V) and Ce(IV) to form microporous silicon, ME Dudley and KW Kolasinki, Electrochemical and solid-state letters, 12(4), D22-D26 (2009).

(Continued)

*Primary Examiner* — Thomas Pham
(74) *Attorney, Agent, or Firm* — Nixon & Vanderhye P.C.

(57) ABSTRACT

A method of making porous silicon using a chemical etchant comprising metal ions is described.

15 Claims, 4 Drawing Sheets

Reaction Exotherm

Time *(min)*

(56) References Cited

U.S. PATENT DOCUMENTS

2008/0138270 A1 6/2008 Li et al.
2009/0258296 A1* 10/2009 Kawasato ............... H01M 4/36
429/223

OTHER PUBLICATIONS

Effects of stain etchant composition on the photoluminescence and morphology of porous silicon, M Nahidi and KW Kolasinki, Journal of the Electrochemical Society, 153 (1) C19-C26 (2006).
Surface chemistry of hydrogen-passivated porous silicon: Oxidation of surface Si—H groups by acetone, LF Rao and JT Yates, US Office of Naval Research, Technical Report A556462, Apr. 12, 1993.
Leigh Canham, Pore Volume (Porosity) in Porous Silicon, Handbook of Porous Silicon (2014), pp. 135-142.
Office Action issued in JP App. No. 2012-543911 mailed Aug. 12, 2014 (with partial translation).
International Search Report for PCT/GB2010/052112, mailed May 11, 2011.
Written Opinion of the International Searching Authority for PCT/GB2010/052112, mailed May 11, 2011.
UK Search Report for GB0922063.3, dated May 13, 2010.
Limaye, S et al., "Scaleable synthesis route for silicon nanocryatal assemblies", Phys. Stat. Sol., vol. 204, No. 5, Apr. 19, 2007, pp. 1297-1301.
Dudley, M.E. et al., "Structure and photoluminescence studies of porous silicon formed in ferric ion containing stain etchants", Physica Status Solidi, vol. 206, No. 6, (Mar. 23, 2009), pp. 1240-1244.
Dudley, M.E. et al., "Stain Etching with Fe(III), V(V), and Ce(IV) to Form Microporous Silicon", vol. 12, No. 4, (Jan. 29, 2009), pp. D22-D26.
Xu, Y. et al., "Properties of light-emitting porous silicon", Journal of Applied Physics, American Institute of Physics, vol. 101, No. 10, (May 18, 2007), pp. 103509-103509.
Kolasinski, K. et al., "Laser assisted and wet chemical etching of silicon nanostructures", Journal of Vacuum Science and Technology: Part A, vol. 24, No. 4, (Jun. 23, 2006), pp. 1474-1479.

* cited by examiner

POROUS SILICON

This application is the U.S. national phase of International Application No. PCT/GB2010/052112, filed 16 Dec. 2010, which designated the U.S. and claims priority to GB Application No. 0922063.3, filed 17 Dec. 2009, the entire contents of each of which are hereby incorporated by reference.

FIELD OF THE INVENTION

This invention relates to, porous silicon, methods for making porous silicon, porous silicon obtainable from said methods and uses of the porous silicon.

BACKGROUND OF THE INVENTION

Porous silicon is found in a variety of applications where its benign nature, electronic and optical properties and entrapment of other materials is desirable.

There are numerous methods available for making porous silicon. For example, and as described in PCT/GB96/01863, bulk crystalline silicon can be rendered porous by partial electrochemical dissolution in hydrofluoric acid based solutions. This etching process generates a silicon structure that retains the crystallinity and the crystallographic orientation of the original bulk material. Hence, the porous silicon formed is a form of crystalline silicon. Broadly, the method involves anodising, for example, a heavily boron doped CZ silicon wafer in an electrochemical cell which contains an electrolyte comprising a 20% solution of hydrofluoric acid in an alcohol such as ethanol, methanol or isopropylalcohol (IPA). Following the passing of an anodisation current with a density of about 50 mA $cm^{-2}$, a porous silicon layer is produced which may be separated from the wafer by increasing the current density for a short period of time. The effect of this is to dissolve the silicon at the interface between the porous and bulk crystalline regions.

Porous silicon may also be made using the so-called stain-etching technique which is another conventional method for making porous silicon. This method involves the immersion of a silicon sample in a hydrofluoric acid solution containing a strong oxidising agent. No electrical contact is made with the silicon, and no potential is applied. The hydrofluoric acid etches the surface of the silicon to create pores. Up until now stain etching has tended to have poor reproducibility, low yield, be strongly exothermic and produce internal surface areas which are significantly lower than those obtained from anodising wafers.

These existing stain etch methods, particularly for making very high porosity silicon, are not very efficient and they tend to be slow. Further, anodisation currently uses relatively expensive silicon wafers. Existing stain etch methods have not proved to be particularly suitable for producing fully porous silicon which also means the porosified silicon will not be fully biodegradable and will not all be converted to silicic acid in-situ. Existing attempts at fully porosifying silicon tend to result in the porous silicon retaining areas of non porous silicon, particularly at the centre of the silicon particle.

There is a continued need for alternative and preferably improved methods for making porous silicon which address at least some of the issues mentioned above.

SUMMARY OF THE INVENTION

The present invention describes the use of a metal salt in combination with hydrogen fluoride in aqueous solution for making porous silicon and preferably at a reduced temperature. More specifically, and according to a first aspect of the present invention, a method is provided of making porous silicon comprising:

contacting elemental particulate silicon with a chemical etchant solution, wherein the chemical etchant solution comprises, or consists of, or consists essentially of hydrofluoric acid and a dissolved metal salt.

The stain etched porous silicon obtained according to the present invention may be characterised over or differentiated from conventionally made stain etched porous silicon by the presence of one or more of the following features: high surface area; high pore volume; a lack of, or substantial lack of silicon regions of largest width 10 nm; fully mesoporous regions at greater than 85 wt %, preferably greater than 95 wt %; the presence of at least one metal, for example, selected from iron, silver, gold, aluminium, platinum, vanadium, copper on the pore wall surface at a concentration in the range of about 0.0001 wt % to 1 wt %; and a high solubility in aqueous liquids such as body fluids. As such, and according to a second aspect, porous silicon obtainable by the method according to the first aspect of the present invention is provided.

The method according to the first aspect of the present invention is suitable for use with particulate silicon feedstock comprising, consisting of, or consisting essentially of spherical or substantially spherical particles and acicular or irregularly shaped silicon microparticles. Advantageously, the sphericity of the porous silicon microparticles produced in accordance with the present invention may be high. According to a further aspect of the present invention, there is provided porous particulate silicon wherein the particulate silicon comprises, consists of, or consists essentially of spherical or substantially spherical particles possessing a surface area of greater than about 150 $m^2/g$, or greater than about 200 $m^2/g$, or greater than about 300 $m^2/g$, or greater than about 400 $m^2/g$, or greater than about 450 $m^2/g$. For example, the surface area may be up to about 500 $m^2/g$, for example up to about 480 $m^2/g$. The surface area may be at least 150 $m^2/g$ or at least 200 $m^2/g$. The spherical or substantially spherical particles made in accordance with the present invention are particularly useful as in-vivo contrast agents for medical imaging. As such, in a further aspect there is provided a method of imaging a human or animal subject, wherein the contrast of the image is enhanced by administering an imaging agent comprising porous silicon in accordance with any one of the aspects of the present invention to the human or animal subject.

There are a number of advantages associated with the present invention and the present invention seeks to provide one or more of the following: fully biodegradable porous silicon; highly porous silicon, for example about 50 to about 70 vol % porosity; high pore volumes, for example up to about 0.5 ml/g; batch sizes up to at least 100 g; throughput of at least 100 g/hour; good yields, for example up to about 60% by weight of the feedstock is converted to porous silicon; porous silicon which may be loaded with high payloads of one or more active materials, for example in amounts greater than about 20 wt %, for example greater than about 40 wt %.

DETAILED DESCRIPTION OF THE INVENTION

Silicon

As used herein, and unless otherwise stated, the term "silicon" refers to solid elemental silicon. For the avoidance of doubt, and unless otherwise stated, it does not include silicon-containing chemical compounds such as silica, silicates or silicones, although it may be used in combination with these materials.

The purity of the silicon may depend to some extent on the final application of the porous silicon. For example, the silicon may be about 95 to 99.99999% pure, for example about 96 to 99.9% pure. Advantageously, so-called metallurgical silicon, which may be suitable in a range of applications, including foodstuffs has a purity of about 98 to 99.5% and is suitable for use in the methods of the present invention.

The physical forms of silicon which are suitable for use in the method according to the present invention may be chosen from or comprise one or more of amorphous silicon, single crystal silicon, metallurgical grade silicon and polycrystalline silicon (including nanocrystalline silicon, the grain size of which is typically taken to be 1 to 100 nm) and including combinations thereof. Any of the above-mentioned types of silicon, which are suitable for use in the present invention, may be porosified to form porous silicon, which may be referred to as "pSi". The silicon may be surface porosified or more substantially porosified. Suitable forms of porous silicon include mesoporous, microporous or macroporous silicon. Microporous silicon contains pores possessing a diameter less than 2 nm; mesoporous silicon contains pores having a diameter in the range of 2 to 50 nm; and macroporous silicon contains pores having a diameter greater than 50 nm.

The surface area and the size of the pores in the silicon may to some extent depend on what application the porous silicon is to be used for. The porous silicon may be loaded with an additional material which is to be delivered to a human or animal subject. For example, the BET surface area of the porous silicon is preferably greater than 200 m$^2$/g for biodegradability. The BET surface area is determined by a BET nitrogen adsorption method as described in Brunauer et al., J. Am. Chem. Soc., 60, p 309, 1938. The BET measurement is performed using a Tristar 3000 Micrometrics instrument. The sample is outgassed under flowing dry nitrogen at 120° C. for 16 hours before measurement. The pore volume is preferably in excess of 0.1 ml/g and is measured by BET analysis using a Tristar 3000 Micromeritics instrument and standard BJH (Barrett Joyner Harlender) analysis of the isotherm, as described in Adsorption, Surface Area and Porosity by S. J. Gregg and K. S. W. Sing, $2^{nd}$ Edition, Academic Press, London.

Preferably, the sphericity of the mesoporous silicon particles is high. The sphericity of the mesoporous silicon particles is the ratio of the surface area of a non-porous sphere with the same volume as the mesoporous silicon particle plus the mesopore volume of the mesoporous silicon particle to the external surface area of the mesoporous silicon particle. The external surface area of the mesoporous silicon particle is the total surface area minus the mesopore surface area. The BET technique is used to measure surface areas and combined with measurements of particle size distributions to calculate the sphericity. The sphericity of an individual particle is given by the following equation:

$$\pi^{1/3}(6V_p)^{2/3}/A_p$$

$V_p$ is the volume of the particle and $A_p$ is the surface area of the particle.

The form of the silicon for use in the method is a powder and may comprise particles of various size. In the present invention, particle size distribution measurements, including the mean particle size ($d_{50}$/μm), $d_{90}$ and $d_{10}$ of the silicon particles are measured using a Malvern Particle Size Analyzer, Model Mastersizer, from Malvern Instruments. A helium-neon gas laser beam is projected through a transparent cell which contains the silicon particles suspended in an aqueous solution. Light rays which strike the particles are scattered through angles which are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and dispersant solution to determine the particle size distribution of the silicon.

Some suitable examples of approximate particle size distribution for representative feedstock samples are provided in the following Table 1.

TABLE 1

| | Particle size distribution | | |
|---|---|---|---|
| Sample | $d_{10}$/μm | $d_{50}$/μm | $d_{90}$/μm |
| 1 | 1 | 10 | 40 or 50 |
| 2 | 0.5 | 2 | 10 |
| 3 | 0.1 | 0.5 | 1 |

Advantageously, the $d_{90}$ of the feedstock may be about 11 μm or less for example about 10 μm or less. The $d_{90}$ of the feedstock may be at least about 5 μm.

Methods for making silicon powders such as silicon microparticles and silicon nanoparticles are well known in the art. Silicon microparticles are generally taken to mean particles of about 1 to 1000 μm in diameter and silicon nanoparticles are generally taken to mean particles possessing a diameter of about 100 nm and less. Silicon nanoparticles therefore typically possess a diameter in the range of about 1 nm to about 100 nm, for example about 5 nm to about 100 nm. Methods for making silicon powders are often referred to as "bottom-up" methods, which include, for example, chemical synthesis or gas phase synthesis. Alternatively, so-called "top-down" methods refer to such known methods as electrochemical etching or comminution (e.g. milling as described in Kerkar et al. J. Am. Ceram. Soc., vol. 73, pages 2879-2885, 1990). PCT/GB02/03493 and PCT/GB01/03633, the contents of which are incorporated herein by reference in their entirety, describe methods for making particles of silicon, said methods being suitable for making silicon feedstocks for use in the present invention. Such methods include subjecting silicon to centrifuge methods, or grinding methods. Suitable sources of nanoparticle silicon may be obtained commercially from SDC materials which possess, for example, an average particle diameter of about 20 nm.

Other examples of methods suitable for making silicon nanoparticles include vaporation and condensation in a subatmospheric inert-gas environment. Various aerosol processing techniques have been reported to improve the production yield of nanoparticles. These include synthesis by the following techniques: combustion flame; plasma; laser ablation; chemical vapour condensation; spray pyrolysis; electrospray and plasma spray. Because the throughput for these techniques currently tends to be low, preferred nanoparticle synthesis techniques include: high energy ball milling; gas phase synthesis; plasma synthesis; chemical synthesis; sonochemical synthesis. The preferred methods of producing silicon nanoparticles are described in more detail.

High-Energy Ball Milling

High energy ball milling, which is a common top-down approach for nanoparticle synthesis, has been used for the generation of magnetic, catalytic, and structural nanoparticles, see Huang, "Deformation-induced amorphization in ball-milled silicon", Phil. Mag. Lett., 1999, 79, pp 305-314. The technique, which is a commercial technology, has traditionally been considered problematic because of contamination problems from ball-milling processes. However, the availability of tungsten carbide components and the use of inert atmosphere and/or high vacuum processes has reduced impurities to acceptable levels. Particle sizes in the range of about 0.1 to 1 μm are most commonly produced by ball-milling techniques, though it is known to produce particle sizes of about 0.01 μm.

Ball milling can be carried out in either "dry" conditions or in the presence of a liquid, i.e. "wet" conditions. For wet conditions, typical solvents include water or alcohol based solvents.

Gas Phase Synthesis

Silane decomposition provides a very high throughput commercial process for producing polycrystalline silicon granules. Although the electronic grade feedstock (currently about \$30/kg) is relatively expensive, so called "fines" (microparticles and nanoparticles) are a suitable waste product for use in the present invention. Fine silicon powders are commercially available. For example, NanoSi™ Polysilicon is commercially available from Advanced Silicon Materials LLC and is a fine silicon powder prepared by decomposition of silane in a hydrogen atmosphere. The particle size is 5 to 500 nm and the BET surface area is about 25 $m^2/g$. This type of silicon has a tendency to agglomerate, reportedly due to hydrogen bonding and Van der Waals forces.

Plasma Synthesis

Plasma synthesis is described by Tanaka in "Production of ultrafine silicon powder by the arc plasma method", J. Mat. Sci., 1987, 22, pp 2192-2198. High temperature synthesis of a range of metal nanoparticles with good throughput may be achieved using this method. Silicon nanoparticles (typically 10-100 nm diameter) have been generated in argon-hydrogen or argon-nitrogen gaseous environments using this method.

Chemical Synthesis

Solution growth of ultra-small (<10 nm) silicon nanoparticles is described in US 20050000409, the contents of which are incorporated herein in their entirety. This technique involves the reduction of silicon tetrahalides such as silicon tetrachloride by reducing agents such as sodium napthalenide in an organic solvent. The reactions lead to a high yield at room temperature.

Sonochemical Synthesis

In sonochemistry, an acoustic cavitation process can generate a transient localized hot zone with extremely high temperature gradient and pressure. Such sudden changes in temperature and pressure assist the destruction of the sonochemical precursor (e.g., organometallic solution) and the formation of nanoparticles. The technique is suitable for producing large volumes of material for industrial applications. Sonochemical methods for preparing silicon nanoparticles are described by Dhas in "Preparation of luminescent silicon nanoparticles: a novel sonochemical approach", Chem. Mater., 10, 1998, pp 3278-3281.

Mechanical Synthesis

Lam et al have fabricated silicon nanoparticles by ball milling graphite powder and silica powder, this process being described in J. Crystal Growth 220(4), p 466-470 (2000), which is herein incorporated by reference in its entirety. Arujo-Andrade et al have fabricated silicon nanoparticles by mechanical milling of silica powder and aluminum powder, this process being described in Scripta Materialia 49(8), p 773-778 (2003).

The particulate porous silicon produced by the above methods may be highly spherical.

The porous silicon formed according to the present invention may be derivatised. Derivatised porous silicon is porous silicon possessing a covalently bound monolayer on at least part of its surface. The monolayer typically comprises one or more organic groups that are bonded by hydrosilylation to at least part of the surface of the porous silicon. Derivatised porous silicon is described in PCT/GB00/01450, the contents of which are incorporated herein by reference in their entirety. PCT/GB00/01450 describes derivatisation of the surface of silicon using methods such as hydrosilylation in the presence of a Lewis acid. In that case, the derivatisation is effected in order to block oxidation of the silicon atoms at the surface and so stabilise the silicon. Methods of preparing derivatised porous silicon are known to the skilled person and are described, for example, by J. H. Song and M. J. Sailor in Inorg. Chem. 1999, vol 21, No. 1-3, pp 69-84 (Chemical Modification of Crystalline Porous Silicon Surfaces). Derivitisation of the silicon may be desirable when it is required to increase the hydrophobicity of the silicon, thereby decreasing its wettability. Preferred derivatised surfaces are modified with one or more alkyne groups. Alkyne derivatised silicon may be derived from treatment with acetylene gas, for example, as described in "Studies of thermally carbonized porous silicon surfaces" by J. Salonen et al in Phys Stat. Solidi (a), 182, pp 123-126, (2000) and "Stabilisation of porous silicon surface by low temperature photoassisted reaction with acetylene", by S. T. Lakshmikumar et al in Curr. Appl. Phys. 3, pp 185-189 (2003).

The surface of the elemental silicon may comprise one or more silicon compounds. For example, at least some of the porous silicon surface may comprise silicon bonded to oxygen to form an oxide layer. The silicon particles may possess an oxide content corresponding to between about one monolayer of oxygen and a total oxide thickness of less than or equal to about 4.5 nm covering the entire silicon skeleton. The porous silicon may have an oxygen to silicon atomic ratio between about 0.04 and 2.0, and preferably between 0.60 and 1.5. Oxidation may occur in the pores and/or on the external surface of the silicon. There may be at least one metal, for example, selected from iron, silver, gold, aluminum, vanadium, platinum, copper surface present on the surfaces of the pore walls at a concentration in the range of about 0.0001 wt % to 1 wt %.

Chemical Etchant

The etchant solution comprises hydrofluoric acid and a metal salt which has been dissolved in the hydrofluoric acid (aqueous solution of hydrogen fluoride). The etchant therefore comprises metal ions, for example iron ions. Suitable examples of metal salts include iron containing salts, particularly ferric chloride ($FeCl_3$). Other suitable metal salts include silver, copper, gold, aluminum, vanadium or platinum containing salts. Suitable anions include chloride, nitrate, oxide or sulphate which may be combined with any of the afore mentioned metals. The metal salt may be vanadium oxide, for example $V_2O_5$. The metal salt may be first dissolved in water to form an aqueous solution before it is combined with the hydrofluoric acid. The molar concentration, or molarity of aqueous solution in which the metal salt has been dissolved may be about 0.012M to about 5.6M, for example about 0.1M to 3M. The concentration of metal ions in the etchant solution may be about 0.01M to 4.7M, for example 0.09M to 2.5M. The ratio of moles of HF to etch 1 mole of silicon may be about 6. The aqueous hydrofluoric acid which is combined with the aqueous solution of dissolved metal salt may be about 1% to about 48%, for example, 40%.

Advantageously, after the hydrofluoric acid and metal salt have been combined to form the etchant solution, and prior to combining the etchant with the particulate silicon, the etchant is chilled to below room temperature. The hydrofluoric acid and/or solution comprising metal ions may be chilled before they are combined. The particulate silicon may also be chilled before addition. The particulate silicon may be added in the form of a chilled slurry, wherein the chilled slurry comprises silicon and water and either metal salt or hydrofluoric acid.

For example, the etchant solution may be at an initial temperature of less than about 0° C., for example less than about −5° C., preferably less than about −10° C. The etchant solution may be at a temperature of about −25° C. to less than about 5° C. or less than about 0° C., for example about −15° C. The etchant solution may be at an initial temperature of about −15° C. to about −25° C.

The etchant and particulate silicon may be stirred on mixing and the temperature may be monitored. During the etching process, the temperature of the solution is typically maintained at below 50° C. Advantageously, the temperature is maintained below 10° C. and more preferably below 0° C. After a period of time, for example about 30 minutes, water, preferably de-ionised water, may be combined with the combined etchant and silicon mixture. Following addition of the water, and preferably immediately, the mixture is filtered to leave a damp powder which may be dried, for example on a hotplate in air. Advantageously, there may be a maximum exotherm occurring between about −5° C. and 5° C. during porosification. The present inventors have found that particularly high surface areas, pore volumes and yields are obtainable under these conditions. Without wishing to be bound by theory, it is believed that chilling and maintaining the electrolyte temperature below about 0° C. minimises the chemical etching of the elemental silicon and allows the electrochemical pore formation to dominate during the process. The reaction exotherm may be monitored using known techniques. For example, it may be monitored using a Lacomit coated temperature probe.

The present inventors have found that it is particularly advantageous to chill the etchant prior to it being combined with the particulate silicon because significantly higher porosities, yields and surface areas may be obtained.

Advantageously, the methods in accordance with the present invention may be used for porosifying less expensive feedstock, for example metallurgical grade silicon. Existing methods of porosifying silicon, particularly anodisation, make use of high purity electronic grade silicon wafers which are significantly more expensive. Also, the present process provides a significantly higher throughput compared to existing methods. For example, about 100 g of porous silicon/hour may be produced.

The process according to the present invention provides a novel stain etched porous silicon. Up until now, it is believed that the best surface area achieved for stain etched porous silicon is of the order of about 140 $m^2/g$ and a pore volume of the order of about 0.3 ml/g. The present invention provides stain etched porous silicon possessing a surface area of greater than about 450 $m^2/g$ and pore volumes greater than about 0.3 ml/g, preferably greater than about 0.5 ml/g. This may optionally be achieved in connection with feedstock comprising highly spherical particles of silicon. Anodisation methods are not suitable for use in connection with such a feedstock.

Stain etched and anodised porous silicon are distinguishable to the skilled person due to the processes involved in these methods. Anodisation requires that the etchant is brought into contact with one side of the highly pure silicon wafer thus resulting in a distinctive morphology of the porous silicon. However, the present invention makes use of particulate silicon, so the etchant is able to etch a silicon particle from all sides. This means that the anodised porous silicon and stain etched porous silicon possess a different morphology which is readily evident to the skilled person. The anodised membrane and thus the resulting porous silicon particles have a very high proportion of "through" pores that traverse from one side of the particle to the other. This is less evident in stain etched particles where more pores do not traverse from one side of the particle to the other and where such pores may be referred to as "dead end" pores. A higher percentage of the pores in material produced by anodisation also have aligned directionality. In stain etched particles, the pores are oriented over a much wider spread of angles relative to one another (up to 180° for a sphere). Pore directionality is also influenced by grain boundaries which are much more prominent in polycrystalline particles subjected to stain etching and not present in single crystal wafers subjected to anodisation.

In the method according to the present invention, the pore morphology may be altered by including a further acid, for example sulphuric acid, in the etch formulation. For example, the addition of a further acid, such as sulphuric acid, may be used to provide one or more of larger surface areas, smaller average pore diameter and larger pore volume when compared to the absence of said further acid. Suitably, this may be achieved by adding 0.2 to 20 vol % of an 18M solution of sulphuric acid to the etchant solution.

Uses of the Porous Silicon

The porous silicon made according to the present invention may be used in numerous applications. Application areas include, but are not limited to, cosmetics, personal care, oral hygiene, medicaments (e.g. drug delivery, including oral drug delivery) and food. Other application areas include in-vivo imaging, diagnostics, fuel cells, batteries, e.g. a lithium battery, catalysts, as a hydrogen reservoir and explosives. Specific product examples which may utilise such materials include, but are not limited to, chocolate, chewing gum and toothpaste.

The porous silicon may be used as a foodstuff in its own right and may, optionally, be loaded with one or more ingredients. The silicon may be loaded such that the one or more ingredients are entrapped by the porous silicon. These ingredients may be selected from one or more of: oxygen sensitive edible oils; minerals; oxygen sensitive fats including dairy fats; oil soluble ingredients; vitamins; fragrances or aromas; flavours; enzymes; probiotic bacteria; prebiotics; nutraceuticals; amino acids; herbal extracts; herbs; plant extracts; edible acids; salt; antioxidants; therapeutic agents.

The porous silicon may be loaded with a pharmaceutical or toxic chemical species for timed release. One or more biological materials, such as bacteria, virus, antigens or other inoculants may be added to the porous silicon for slow release to affect biological control and treatment.

The porous silicon may be used in a dentifrice composition such as a toothpaste, tooth powder, gum or oral gel. It may be present as an abrasive and/or for delivering one or more entrapped ingredients. The dentifrice composition will comprise constituents well known to one of ordinary skill;

these may broadly be characterised as active and inactive agents. Active agents include anticaries agents such as fluoride, antibacterial agents, desensitising agents, antitartar agents (or anticalculus agents) and whitening agents. Inactive ingredients are generally taken to include water (to enable the formation of a water phase), detergents, surfactants or foaming agents, thickening or gelling agents, binding agents, efficacy enhancing agents, humectants to retain moisture, flavouring, sweetening and colouring agents, preservatives and, optionally further abrasives for cleaning and polishing.

The mesoporous silicon may be used as a biodegradable contrast agent for medical imaging purposes within animal or mammalian tissues. In particular, the metal content of mesoporous silicon particles may be tuned to improve X-ray contrast. The porosity of the mesoporous silicon particles may be tuned to improve ultrasound contrast. The particle size distribution may be tuned to optimise biodistribution within the tissues. The sphericity of the mesoporous silicon particles is preferably high in order to lower the contrast dependence on viewing angle or to improve transport within the vasculature.

The afore mentioned uses when used in connection with porous silicon made using conventional techniques are described in the following references. "Three dimensional porous silicon particles for use in high performance lithium secondary batteries" by H. Kim et al in Angew. Chem. Int. Ed. 47, 10151-10154 (2008). "Combustion performance of porous silicon-based energetic compositions" by B. A. Mason et al in Proc of 45th AIAA/ASME/SAE/ASEE Joint Propulsion Conference, 2-5 Aug. 2009, Denver, Colo., USA. "Investigating nanoporous silicon explosive devices" by M. du Pleiss in Phys. Status. Solidi. C6 (7) 1763-1768 (2009). "Hybrid metal/silicon nanocomposite systems and their catalytic activity" by S. Polisski et al. in Phys. Status. Solidi. C6(7) 1575-1579 (2009). "Use of powders and composites based on porous and crystalline silicon in the hydrogen power industry" by A. I. Manilov et al. in Ukr. J. Phys. 55(8) 928-935 (2010). "Biomedical applications of nanostructured porous silicon: a review" by R. J. Martin-Palma et al. in J. Nanophotonics 4, 042502 13 Sep. 2010. "Mesoporous silicon in drug delivery applications" by J. Salonen et al. in J. Pharm. Sci. 97 (2) 632-653 (2008). "Mesoporous silicon: a platform for the delivery of therapeutics" by C. A. Prestidge et al. in Expert Opin. Drug Deliv. 4(2) 101-110 (2007). "Nanoscale semiconducting silicon as a nutritional food additive" L. T. Canham in Nanotechnology 18, 185704 (2007).

BRIEF DESCRIPTION OF THE DRAWINGS

Embodiments of the invention will now be described, by way of example only and without limitation, with reference to the accompanying drawings and the following Examples, in which.

EXAMPLES

Example 1

Figure 1:
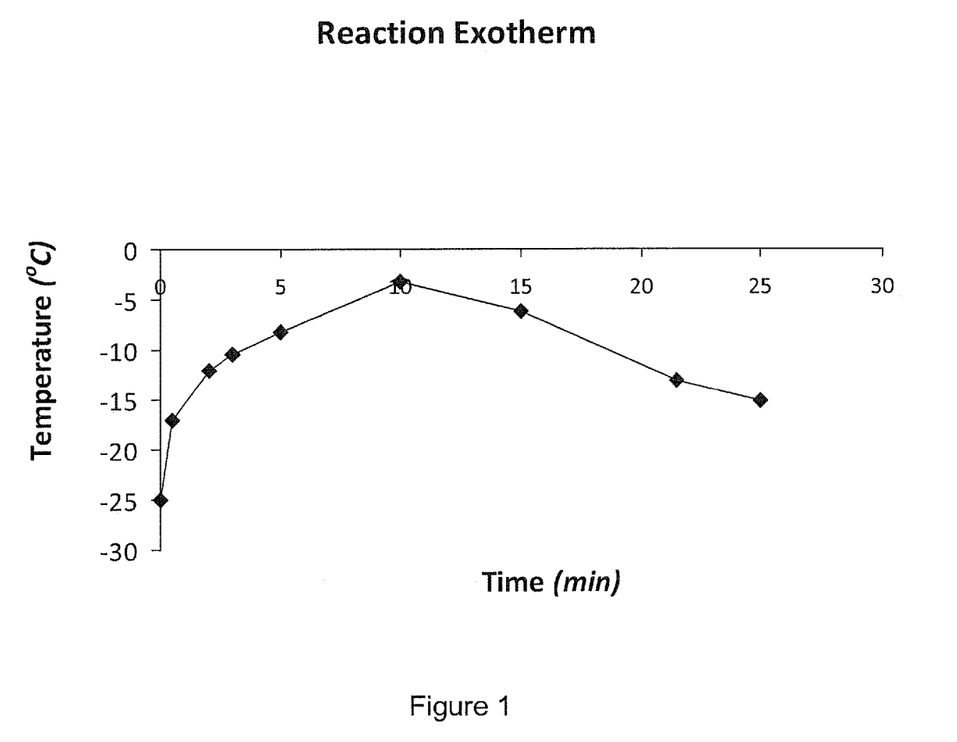
FIG. 1 illustrates a reaction exotherm for Example 1.

600 ml of 1.85M (aqueous) ferric chloride solution was added to 120 ml of 40% (aqueous) hydrofluoric acid. The resulting solution was chilled to −25° C. and poured into a 2 L polyethylene bottle containing 10 g of metallurgical-grade silicon powder ($d_{10}$=0.71 μm, $d_{50}$=2.10 μm, $d_{90}$=8.9 μm). The bottle was returned to the chilling bath (−25° C.), covered and stirred with an acid-resistant screw-propeller stirring rod (~400 rpm). The temperature was monitored in accordance with FIG. 1. At t=~30 min, 500 ml of de-ionised water (room temperature) was added to the mixture and the diluted mixture immediately poured into a large-area PTFE vacuum-filtration vessel containing a 10 μm MITEX filter membrane. The mixture was filtered until a damp powder remained on the membrane (the filter time was 19 min). The membrane/powder was removed and dried on a hotplate at 45° C. for 24 hr, in air and the resulting powder was weighed. This gave a 23.7% yield of porous silicon which possessed: a surface area=479.7 $m^2/g$, an average pore volume=0.52 ml/g; an average pore diameter=3.8 nm.

Example 2

Figure 2:
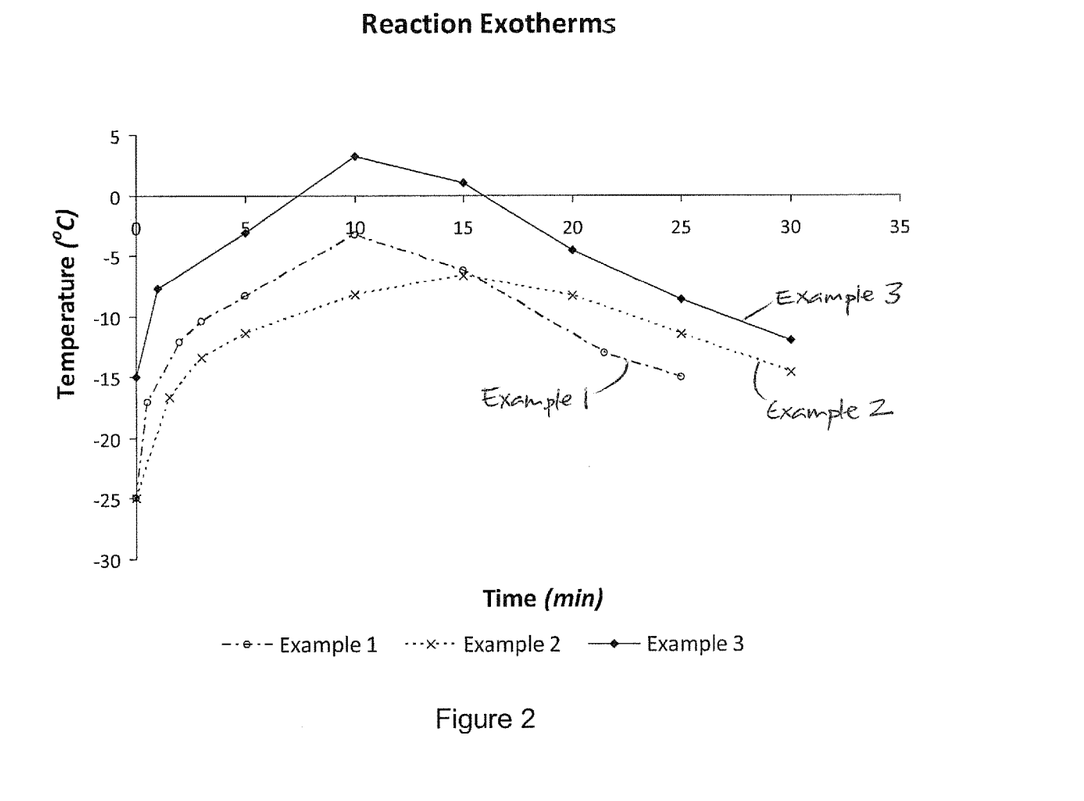
FIG. 2 illustrates reaction exotherms for Examples 1-3.

600 ml of 1.85M (aqueous) ferric chloride solution was added to 120 ml of 40% (aqueous) hydrofluoric acid. The resulting solution was chilled to −25° C. and poured into a 2 L polyethylene bottle containing 10 g of metallurgical-grade silicon powder ($d_{10}$=0.71 μm, $d_{50}$=2.10 μm, $d_{90}$=8.9 μm). The bottle was returned to the chilling bath (−25° C.), covered and stirred with an acid-resistant screw-propeller stirring rod (~400 rpm). The temperature was monitored in accordance with FIG. 2. At t=~30 min, 500 ml of de-ionised water (room temperature) was added to the mixture and the diluted mixture immediately poured into a large-area PTFE vacuum-filtration vessel containing a 10 μm MITEX filter membrane. The mixture was filtered until a damp powder remained on the membrane (the filter time was 15 min). The membrane/powder was removed and dried on a hotplate at 45° C. for 24 hr, in air and the resulting powder was weighed. This gave a 40.3% yield of porous silicon which possessed: a surface area=141.2 $m^2/g$, an average pore volume=0.305 ml/g; an average pore diameter=6.8 nm.

Example 3

600 ml of 1.85M (aqueous) ferric chloride solution was added to 120 ml of 40% (aqueous) hydrofluoric acid. The resulting solution was chilled to −15° C. and poured into a 2 L polyethylene bottle containing 10 g of metallurgical-grade silicon powder ($d_{10}$=0.71 μm, $d_{50}$=2.10 μm, $d_{90}$=8.9 μm). The bottle was returned to the chilling bath (−15° C.), covered and stirred with an acid-resistant screw-propeller stirring rod (~400 rpm). The temperature was monitored in accordance with FIG. 2. At t=~30 min, 500 ml of de-ionised water (room temperature) was added to the mixture and the diluted mixture immediately poured into a large-area PTFE vacuum-filtration vessel containing a 10 μm MITEX filter membrane. The mixture was filtered until a damp powder remained on the membrane (the filter time was 14 min). The membrane/powder was removed and dried on a hotplate at 45° C. for 24 hr, in air and the resulting powder was weighed. This gave an 18.7% yield of porous silicon which possessed: a surface area=359.6 $m^2/g$, an average pore volume=0.463 ml/g; an average pore diameter=4.4 nm.

Example 4

The dissolution of porous silicon prepared via a number of routes was carried out under sink condition. 5.5 mg of porous silicon powder were placed in a plastic bottle with 200 ml of trizma buffer of pH 7.4. The bottle was placed in a water bath set at 37° C. and the mixture stirred at 46 rpm. The dissolved silicon (as an orthosilicic acid in a solution) was quantitatively determined spectrophotometrically using a molybdenum blue assay. The molybdenum blue assay was undertaken by withdrawing 2.5 ml of solution at specific time periods (24 hours) and was replaced with 2.5 ml of medium (trizma buffer). The solution was filtered with a 0.45 μm syringe filter. To 2.5 ml of filtered solution, the following solutions were added:
1. 0.6 ml of 0.25M HCl to acidify the sample.
2. 1.25 ml 1% w/v EDTA to complex interfering metal ions.
3. 1.25 ml of 5% w/v ammonium molybdate which reacts with HCl to form molybdic acid and in turn forms silicon molybdenum acid.
4. 2.5 ml of 17% w/v sodium sulphite which reduces the silicon molybdenum acid to form Mo-blue $H_2Si(Mo_2O_7)_6$.

The absorbance of the resulting solution was measured at y=700 nm using a spectrophotometer.

Mesoporous silicon powder of 70% porosity, prepared via the wafer anodisation process showed 74% dissolution over 24 hrs within the above in-vitro sink dissolution conditions and complete (100%) biodegradability over significantly longer periods.

Stain etched material, prepared by a known route comprising the use of $HF/HNO_3$ to etch powder without electrolyte cooling, typically showed <10% dissolution over 24 hrs within the above in-vitro dissolution conditions and incomplete (<90%) biodegradability over much longer periods.

Metal assisted etch material of the present invention typically showed 20-40% dissolution over 24 hrs within the above in-vitro dissolution conditions, and hence higher biodegradability than prior art material.

Example 5

The effect of particle size on BET surface area and pore volume was determined for two feedstock samples of metallurgical silicon (Sample A and Sample B). For Sample A (99.1 wt % Si, 0.185 wt % Al, 0.48 wt % Fe), $d_{10}$=2.4 μm, $d_{50}$=8.6 μm, $d_{90}$=46 μm. For Sample B (99.4 wt % Si, 0.1 wt % Al, 0.3 wt % Fe), $d_{10}$=1.0 μm, $d_{50}$=3.7 μm, $d_{90}$=10.9 μm.

Figure 3:
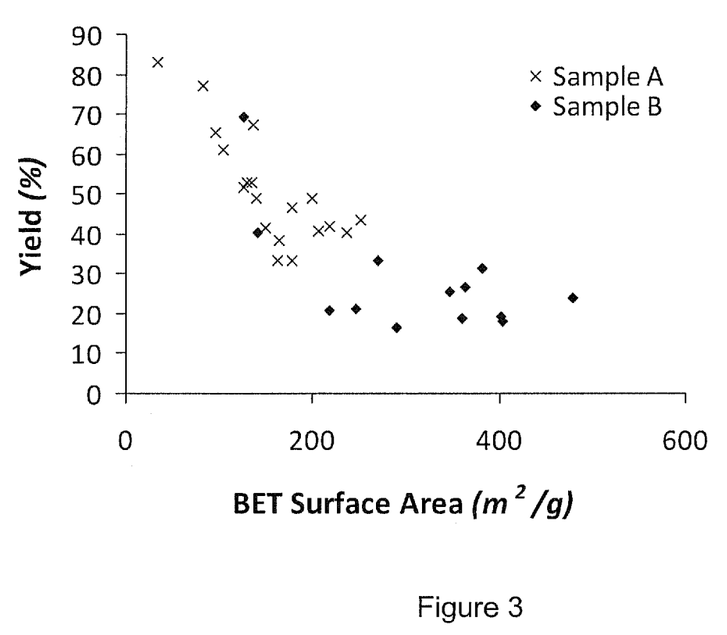
FIG. 3 illustrates yields and surface areas obtained for Example 5.

Stain-etching was carried out with 10 g batches of silicon powder. The HF volumes were fixed to give a molar ratio [HF]/[Si]=7.6. 600 ml of 1.85M $FeCl_3$ solution and 120 ml of 40% HF were combined. The HF was electronic grade (40%) obtained from OM Group and the $FeCl_3$ was anhydrous iron chloride obtained from Merck. Stock oxidant solutions of 1.85M were prepared by dissolving the ferric chloride in de-ionised water to which was added the 40% HF. Once mixed and chilled to −15 to −25° C. (using a chiller with 1:1 ethylene glycol:water coolant), the solution was poured into a vessel containing the silicon powder and stirred, the vessel being held within the chiller during reaction. The temperature exotherm of each reaction was monitored and after etching the solution was filtered and the powder dried at 50° C. for several hours. The time taken to filter was also recorded, as etching can continue during this process, even after quenching with de-ionised water. Surface area and pore volume measurements were carried out using nitrogen gas adsorption. The averaged and highest product parameters are listed in Table 2 and enables trends between the two feedstocks to be analysed. Results are shown for an average of 21 samples for Sample A and 25 samples for Sample B. The highest values are shown in parenthesis. FIG. 3 is a scatter plot of the yields and surface areas obtained.

TABLE 2

| Sample | Yield (%) | BET Surface Area (m$^2$/g) | Pore volume (ml/g) | Equivalent Porosity (%) |
|---|---|---|---|---|
| A | 43.3 (45.3) | 164 (252) | 0.17 (0.21) | 28.3 (32.6) |
| B | 23.7 (25.7) | 325 (480) | 0.4 (0.52) | 48.2 (54.7) |

As can be seen from Table 2, the feedstock (Sample B) possessing the smaller $d_{90}$ results in significantly higher surface areas and pore volumes.

Example 6

The suitability of using vanadium for porosifying metallurgical grade silicon powder was investigated. The metallurgical grade silicon powder (99.4 wt % Si) possessed a $d_{50}$=1.0 μm, $d_{50}$=3.7 μm and $d_{90}$=10.9 μm. 520 ml of a mixture of 40% HF (260 ml) and deionised water (260 ml) was prepared; the molar ratio [HF]/[Si] was 8.22. $V_2O_5$ (RECTAPURE grade) was dissolved in 40% HF (electronic grade, obtained from OM Group) prior to the addition of water. Following mixing and chilling to a pre-etch temperature between −19° C. and −23° C. the solution was poured into a vessel (2 L polypropylene) containing the silicon powder and stirred. The temperature was monitored and after a 10 minute etch the solution was filtered and the powder dried at 50° C. for several hours. Surface area and pore volume measurements were carried out using nitrogen gas adsorption. In Examples 1 to 3, the particle size measurements are as provided by the manufacturer. In Examples 5 and 6 the particle size measurements are as measured.

Figure 4:
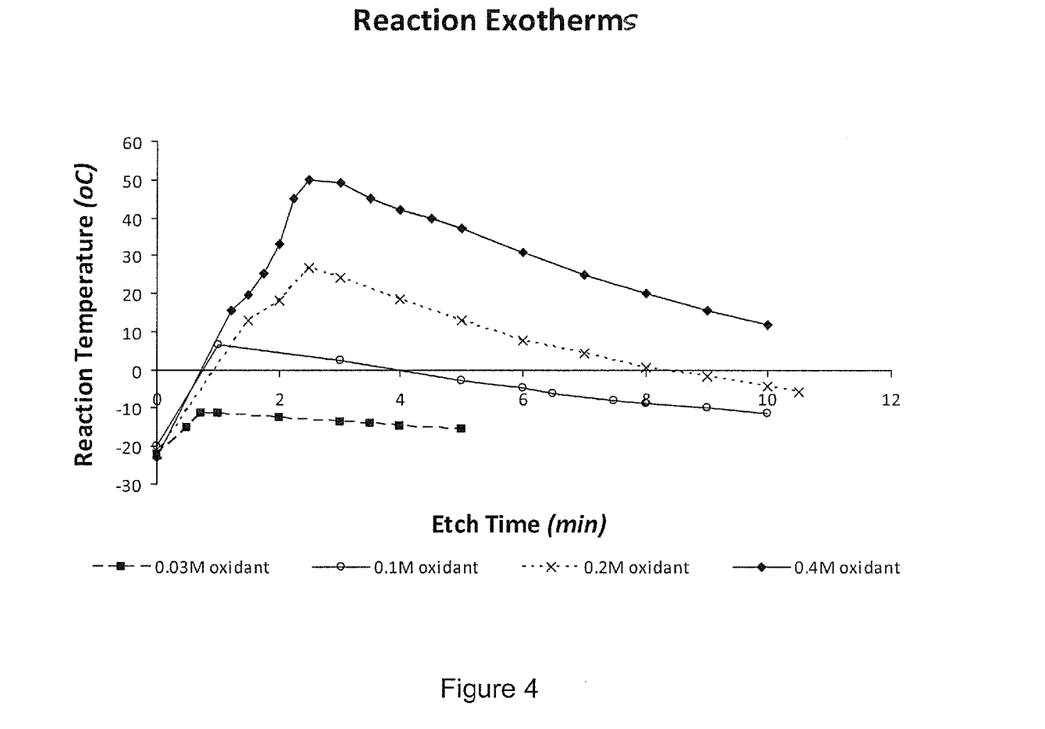
FIG. 4 illustrates reaction exotherms for Example 6.

The reaction process was found to be extremely rapid. Each reaction exotherm peaked typically after 1 min to 3 min, depending on the oxidant concentration used (see FIG. 4).

The results obtained of the BET analysis are shown in Table 3 for five samples (Samples 1-5) of silicon powder (10 g per sample) and one sample (Sample 6) of 20 g of silicon powder. The single 20 g batch was run with the amounts of reagents scaled up (520 ml 40% HF and 520 ml deionised water).

TABLE 3

| Sample | Moles of $V_2O_5$ | Yield (%) | BET Surface Area (m$^2$/g) | Pore volume (ml/g) | Pore Diameter (nm) | Equivalent Porosity (%) |
|---|---|---|---|---|---|---|
| 1 | 0.03 | 82.0 | 17.5 | 0.055 | 11.2-12.2 | 11.3 |
| 2 | 0.1 | 67.9 | 49.9 | 0.118 | 7.6-9.4 | 21.5 |
| 3 | 0.2 | 43.1 | 55.4 | 0.129 | 7.6-9.2 | 23.1 |
| 4 | 0.2 | 46.7 | 45.6 | 0.097 | 7.5-8.5 | 18.4 |
| 5 | 0.4 | 10.3 | 40.6 | 0.112 | 10.0-11.0 | 20.7 |
| 6 | 0.2 | 60.0 | 35.4 | 0.088 | 8.7-9.1 | 17.0 |

The results obtained indicate that the surface areas, yields and pore volumes achieved using $FeCl_3$ are higher than those obtained using the $V_2O_5$.

The invention claimed is:
1. A method of making porous silicon possessing a porosity of about 50 to about 70 vol % comprising contacting elemental particulate silicon with an aqueous chemical etchant, wherein the chemical etchant comprises hydrofluoric acid and a dissolved metal salt and wherein the method comprises cooling the chemical etchant to about −25° C. to about −15° C. before it is contacted with the elemental particulate silicon.

2. A method according to claim 1, wherein during contact with the elemental particulate silicon, the temperature of the chemical etchant is maintained below 10° C.

3. A method according to claim 2, wherein the temperature is maintained below 0° C.

4. A method according to claim 1, wherein the metal salt is ferric chloride ($FeCl_3$).

5. A method according to claim 1, wherein the chemical etchant is cooled to about −15° C.

6. A method according to claim 1, wherein the chemical etchant further comprises sulphuric acid.

7. A method according to claim 1, wherein following porosification of the elemental particulate silicon, water is added and the mixture is filtered and dried.

8. A method according to claim 1, wherein the porous silicon is mesoporous silicon.

9. A method according to claim 1, wherein the d90 of the elemental particulate silicon is about 11 μm or less.

10. A method according to claim 1, wherein the porous silicon is further processed for use in a foodstuff, a consumer care product, an electronic device, in a lithium battery, as a hydrogen reservoir, as an explosive material, as a catalyst or a medicament.

11. A method according to claim 1, wherein the d90 of the elemental particulate silicon is about 10 μm or less.

12. A method of making porous silicon comprising contacting elemental particulate silicon with an aqueous chemical etchant, wherein the chemical etchant comprises hydrofluoric acid and a dissolved metal salt and wherein the method comprises cooling the chemical etchant to about −25° C. to about −15° C. before it is contacted with the elemental particulate silicon and wherein the d90 of the elemental particulate silicon is about 11 μm or less.

13. A method according to claim 12 wherein the porous silicon possesses a porosity of about 50 to about 70 vol %.

14. A method according to claim 12 wherein the d90 of the elemental particulate silicon is between about 5 μm and about 11 μm.

15. A method of making porous silicon, wherein the porous silicon possesses a porosity of about 50 to about 70 vol %, comprising contacting elemental particulate silicon with an aqueous chemical etchant, wherein the chemical etchant comprises hydrofluoric acid and a dissolved metal salt and wherein the method comprises cooling the chemical etchant to about −25° C. to about −15° C. before it is contacted with the elemental particulate silicon and wherein the d90 of the elemental particulate silicon is between about 5 μm and about 11 μm or less.

* * * * *